United States Patent [19]
Ito

[11] Patent Number: 5,154,677
[45] Date of Patent: Oct. 13, 1992

[54] METHOD OF AND APPARATUS FOR MEASURING INSTANTANEOUS POWER

[75] Inventor: Masao Ito, Tokyo, Japan

[73] Assignee: Combi Corporation, Tokyo, Japan

[21] Appl. No.: 498,128

[22] Filed: Mar. 23, 1990

[30] Foreign Application Priority Data

Oct. 7, 1989 [JP] Japan ................................. 1-262808

[51] Int. Cl.$^5$ .................... A63B 71/00; A61B 5/00
[52] U.S. Cl. .............................. 482/8; 482/57; 482/9; 482/900
[58] Field of Search ............. 272/73 DIG. 6, DIG. 5; 73/379; 128/774, 782; 364/506, 511, 413.04; 482/8, 57

[56] References Cited

U.S. PATENT DOCUMENTS

| | | | |
|---|---|---|---|
| 3,744,797 | 7/1973 | Gause et al. | 272/73 |
| 3,845,663 | 11/1974 | Blomberg et al. | 272/73 X |
| 3,845,756 | 11/1974 | Olsson | 272/73 X |
| 4,409,992 | 10/1983 | Sidorenko et al. | 272/DIG. 6 X |
| 4,463,433 | 7/1984 | Hull et al. | 73/379 X |
| 4,976,424 | 12/1990 | Sargeant et al. | 272/DIG. 6 X |

FOREIGN PATENT DOCUMENTS 0255621 2/1988 European Pat. Off. .
8101507 6/1981 Int'l Pat. Institute .

OTHER PUBLICATIONS

"Measurement of work and power output using friction-loaded cycle ergometers" by H. K. A. Lakomy, ERGOMETERS, 1986, vol. 29, No. 4, pp. 509-517.

Primary Examiner—Richard J. Apley
Assistant Examiner—Glenn E. Richman
Attorney, Agent, or Firm—Sughrue, Mion, Zinn, Macpeak & Seas

[57] ABSTRACT

A method and apparatus for measuring instantaneous power resulting from a person pedaling a bicycle ergometer. The rotational speed of a rotary member is periodically detected over a brief period of time at time points corresponding to the start of increase and the end of increase of the rotational speed. From these speeds and time points, the instantaneous power is determined.

19 Claims, 6 Drawing Sheets

METHOD OF AND APPARATUS FOR MEASURING INSTANTANEOUS POWER

BACKGROUND OF THE INVENTION

This invention relates to a method of and an apparatus for measuring the physical strength of a person, and more particularly to a method of and an apparatus for measuring the instantaneous power exerted by a person in a highly safe manner and on the basis of a power theory, without imposing an excessive burden on the subject.

Recently, an increased interest in physical strength has been aroused, and there has now been a demand for a method of and apparatus for measuring such physical strength easily and safely.

The following questions have been posed with respect to conventional physical strength tests, such as, for example a vertical jump test, a reciprocal jump test and a dorsal muscle test.

(1) Since various functions are appraised separately, it is difficult to link the test results with a synthetic appraisal.

(2) Appraisal standards are ambiguous. For example, with respect to a vertical jump, the appraisal standard is the height to which one can jump; however, this is an index of the performance, and is an indirect and subjective one.

(3) There is no standardized scientific proof.

(4) Unusual movements are involved, and the load involved is large, and injuries are liable to occur.

In connection with the above items (1) to (3), it is useful to study the standardization of the indices of physical strength by the power theory. According to power theory, physical strength is measured as the capacity of energy (integrated value of the power), or the power is measured as indices. Forms of development of power are classified according to energy developing mechanisms in a living body, and with respect to each development form, the upper limit value of the power is measured while maintaining the corresponding energy developing mechanism, and this is used as an index of the physical strength in the corresponding energy developing mechanism. Specifically, the measurements are carried out in the following manner:

| (a) | Oxygen-present energy mechanism | |
|---|---|---|
| | Duration: | Infinite |
| | Appraisal of upper limit power: | Power available at 75% of the maximum heat rate, etc. |
| | Main factor for energy generation: | Oxygen |
| (b) | Lactic acid-type anoxia energy mechanism | |
| | Duration: | About 30 seconds |
| | Appraisal of upper limit power: | Average power, critical power, etc. |
| | Main factor for energy generation: | Glycogen |
| (c) | Non-lactic acid-type anoxia energy mechanism | |
| | Duration: | About 7 seconds |
| | Appraisal of upper limit power: | The optimum value determined by speed and developing force of the peak power around approximately 5 to 6 seconds |
| | Main factor for energy generation: | ATP-CP type chemical energy. |

The measurement by a bicycle ergometer based on the power theory has also been proposed or put into practice.

A technique in connection with the above energy mechanisms (a) and (c) has been proposed by Combi Corporation (Japanese Patent Examined Publication No. Hei. 1-42694), and there are known "Aerobike" and "Power max" (both of which are registered and pending trademarks of Combi Corporation; the former is Japanese Trademark Registration No. 1840771, and the latter is Japanese Trademark Publication No. 61-42348) to which the above technique is applied. As to the energy mechanism (b), the Wingate test is known. Such power measurement utilizing a bicycle ergometer is desirable in that the pedaling motion can be said to be analogous to a running motion, the chance of injury is reduced because of a rhythmical motion, the power can be produced efficiently, and bicycling has long been popular.

SUMMARY OF THE INVENTION

As described in detail hereinafter, the present invention resides in measuring instantaneous power (that is, initial power or starting power in the energy mechanism (c)) by the use of a bicycle ergometer, on the basis of the power theory. Such technical concept has not heretofore been known.

More specifically, in the measurement by the non-lactic acid-type anoxia energy mechanism (c), which is known as a short-time power measurement, the power is appraised immediately before the energy is exhausted, that is, 5 to 6 seconds after pedaling is started. On the other hand, in the present invention, the power at the time of starting, that is, within 5 seconds, is measured. In addition, in the measurement by the non-lactic acid-type anoxia energy mechanism (c), the results of the calculated power are subjected to variations when the measurement unit for power calculation is shortened, and therefore the measurement unit is long on the order of not less than 0.5 seconds. However, in the present invention, as later described, the power measurement calculation is carried out during the time from the start of the kicking of the pedal to the end of the pedal kicking, and therefore the measurement time unit is within 0.5 seconds. Accordingly, instead of the appraisal of the average power over a long time, the appraisal of a localized power can be done.

The present invention has been made in view of the foregoing, and an object of the invention is to provide a method of and an apparatus for measuring instantaneous power based on the power theory, utilizing a bicycle ergometer. Therefore, the present invention is proved theoretically, and it is expected that a simple and safe measurement can be carried out.

Another object is to provide a method and an apparatus in which a full-power pedaling time is short, on the order of within 5 seconds, as compared with the power measurement by the conventional non-lactic acid-type anoxia energy mechanism, thus considerably reducing the burden on the subject, and the instantaneous power is measured in a more optimal manner based on the peak value of the power around 2 seconds after the start of the pedaling.

In the present invention, in order to achieve the above objects, there is used a bicycle ergometer equipped with an inertia mechanism having an inertia with respect to a rotational driving movement. The rotational speed of a rotary member of said bicycle ergometer is measured at predetermined short time intervals. In accordance with the measurement value of the rotational speed, a lapsed time between a point of start of increase of the rotational speed and a point of end of increase thereof, and a finite difference of said lapsed time are found, and also the rotational speed between said point of start of increase and said point of end of increase during said lapsed time is found as an average rotational speed. In accordance with these calculated values, the power with respect to said inertia mechanism is determined, and in accordance with this power, the instantaneous power is appraised.

Also, in the present invention, a regression formula with respect to the average rotational speed of a finite difference of said lapsed time as well as a regression formula with respect to the average rotational speed of a finite difference of said rotational speed are found, and the power with respect to said inertia mechanism is obtained by these regression formulas as a function of said average rotational speed, and the maximum value of the power with respect to said inertia mechanism is calculated by the function. With this arrangement, errors due to variations in pedaling, etc., can be removed, thereby providing an accurate measurement of the instantaneous power.

Further, in the present invention, the brake torque is positively used, so that the instantaneous power can be measured accurately in a wide variety of forms.

BRIEF DESCRIPTION OF THE DRAWINGS

FIG. 6 is a view showing the angular position of rotation of similar pedals 1a.

DETAILED DESCRIPTION OF THE PREFERRED EMBODIMENT

A preferred embodiment of the invention will now be described with reference to the drawings.

First, the principle of the measurement will be described, referring to the general construction of an apparatus of this embodiment.

A. Principle of Measurement

Figure 1:
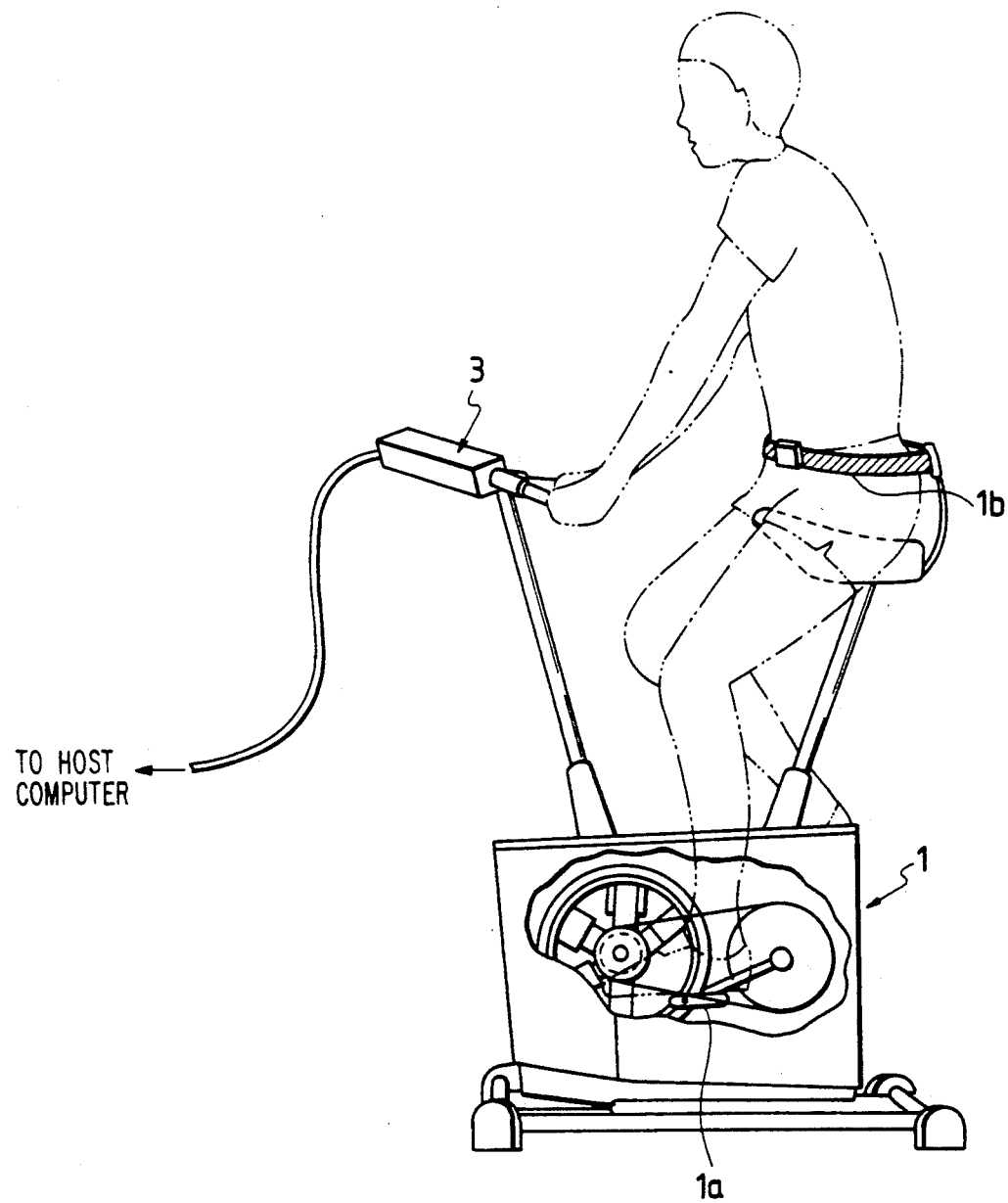
FIG. 1 is a diagrammatical view showing the overall construction of a preferred embodiment of the present invention.

FIG. 1 shows the overall construction of the apparatus of this embodiment. A bicycle ergometer 1 includes a load device unit 2 (FIG. 3), which makes use of eddy current loss. A brake torque is adapted to be applied to pedals 1a. A control box 3 is mounted on the front of the bicycle ergometer 1 (for example, at a handle). The load device unit 2 feeds a signal representative of the rotational speed of the pedal 1a to the control box 3, and in accordance with this signal, the control box 3 displays an appraisal value of an instantaneous power, etc. The control box 3 also feeds a control signal to the load device unit 2 so as to adjust the brake torque. Detailed construction and operation of the control box 3 will be described later.

A belt 1b or the like is attached to a saddle of the bicycle ergometer 1, so that the subject is not allowed to pedal in a standing-up condition, so as to ensure an accurate measurement.

Figure 4A:
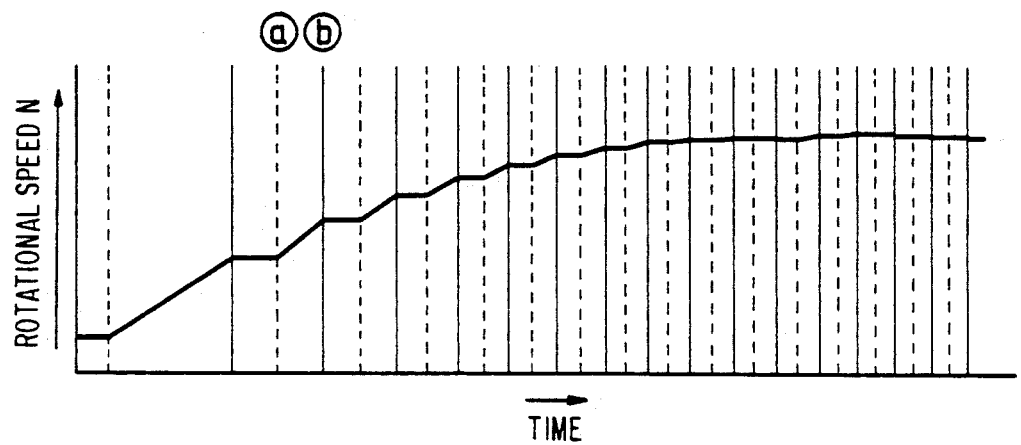
FIGS. 4(A), 4(B), 5(A), 5(B), 7(A), 7(B) and 7(C) are graphs showing the measurement principles of the embodiment of FIG. 1.
Figure 4B:
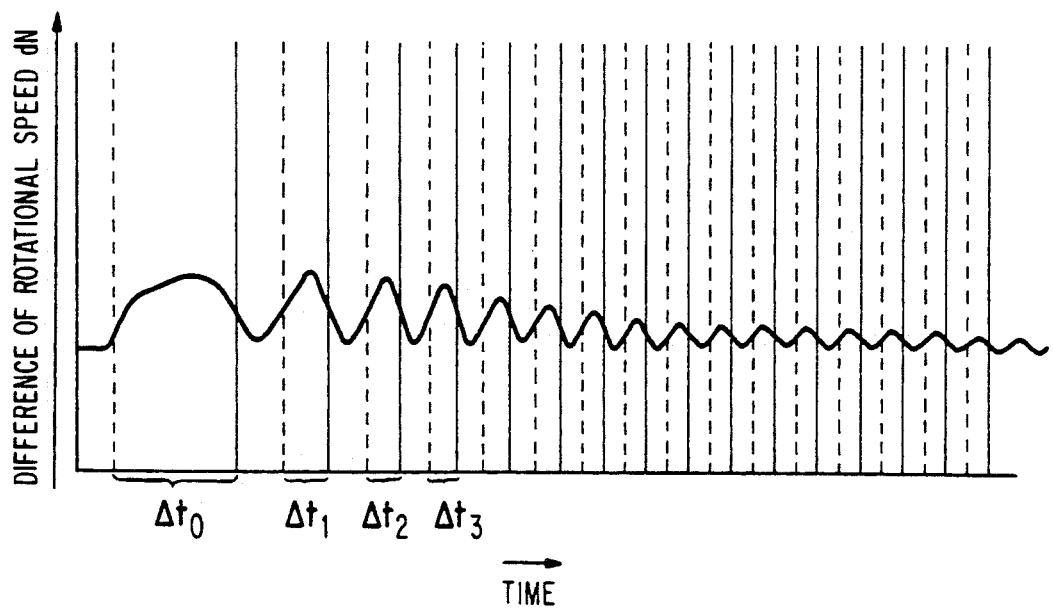

When the subject pedals the bicycle ergometer 1 of FIG. 1 at full power in order to make a measurement of instantaneous power, the measurement value of the rotational speed of the pedal 1a varies, for example, as indicated by (a) (point of start of increase of the rotational speed) and (b) (point of end of increase of the rotational speed) in FIG. 4A. The measurement value of the time difference (differential) with respect to the rotational speed of the pedal 1a varies as shown in FIG. 4B.

As is conventionally known, the peak of the power appears around 2 seconds after the start of a full-power pedaling of a bicycle ergometer, and a stable uniform motion is obtained 4 to 5 seconds after the start. It is known that the instantaneous value of the power peak appearing at this time varies significantly under the influence of the inertia. Therefore, conventionally, the power is calculated from the rotational speed and the brake force, obtained 4 to 5 seconds after the above start (when the influence of the inertia becomes small), and this calculated power is appraised as the non-lactic acid-type anoxia power. However, for appraising the instantaneous power, it is more desirable to use the power of the starting peak. Because of the analogousness to a running motion, this peak power corresponds to the start of a dash in a short-distance run.

In this embodiment, the full-power pedaling is done for only 4 to 5 seconds after the start, and the rotational speed of the pedal 1a during that time is properly analyzed, thereby accurately calculating the peak power.

Figure 5A:
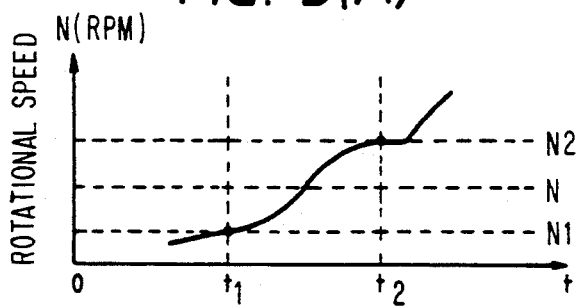
Figure 5B:
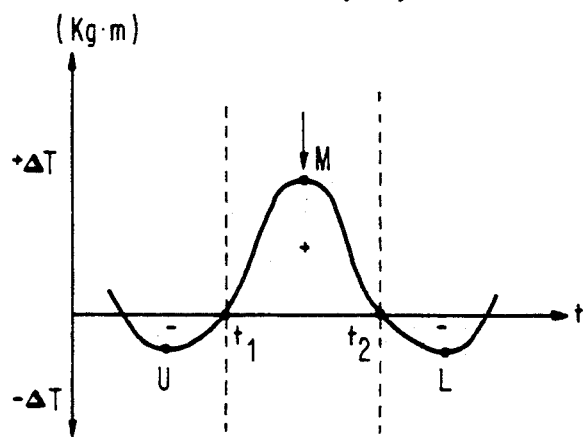

FIG. 5 shows the torque used for accelerating the inertia mechanism of the bicycle ergometer 1 when driving the pedal 1a from a point near to an upper dead point U to a point near to a lower dead point L against the brake torque. More specifically, FIG. 5B diagrammatically shows the torque obtained by subtracting the brake torque from the torque applied by the subject to the crank of the pedal 1a in the rotational direction, and FIG. 5A diagrammatically shows the rotational speed of the pedal 1a.

Here, when an equation of the rotational motion is applied to the bicycle ergometer having the inertia, the following is established:

$$J \cdot \frac{d\omega}{dt} = T - T_l \quad (1)$$

where J represents a moment of inertia (kg.m.s²) of a flywheel on a part of the pedal, $\omega$ represents the angular velocity (rad/s) of the pedal, T represents the torque (kgm) applied to the crank by the subject in the rotational direction, and $T_l$ represents the brake torque (kgm) on the pedal.

The formula (1) is modified into the following formula (2):

$$k \cdot \frac{dN}{dt} = \Delta T \quad (2)$$

where N represents the number of revolutions (rpm) of the pedal 1a, $\Delta T$ is equal to $T - T_l$, and k is equal to $(2\pi/60)J$.

Figure 6:
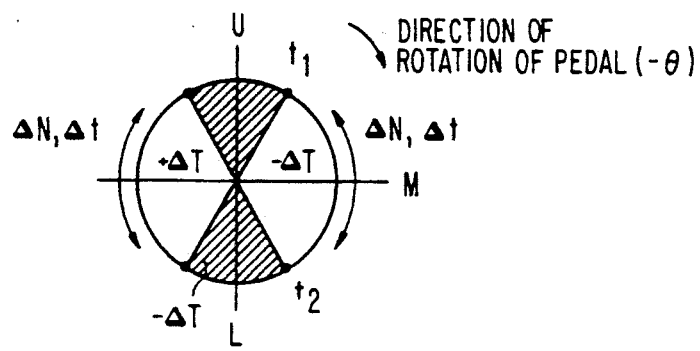

As shown in FIG. 6, $\Delta T$ becomes positive at time t1 immediately after the upper dead point U, and becomes negative at time t2 immediately after the lower dead point L. The formula (2) is integrated between the time t1 and the time t2 to obtain the following formula:

$$k \cdot \int_{t1}^{t2} dN = \int_{t1}^{t2} \Delta T \cdot dt$$

Then, $N(t2) - N(t1) = \Delta N$, and $t2 - t1 = \Delta t$ are provided, and both sides of $$k \cdot \Delta N = \int_{t1}^{t2} \Delta T \cdot dt$$

is divided by $\Delta t$, thereby obtaining the following:

$$k \cdot \frac{\Delta N}{\Delta t} = \frac{\int_{t1}^{t2} \Delta T \cdot dt}{\Delta t}$$

The following is established:

$$\frac{\int_{t1}^{t2} \Delta T \cdot dt}{\Delta t} = \overline{\Delta T}$$

Therefore, the following is established:

$$k \cdot \frac{N}{t} = \overline{\Delta T} \quad (3)$$

It will be appreciated from the above formulas that the average value of the torque which the subject applies for accelerating the bicycle ergometer 1 can be found by measuring the rotational speed of the pedal 1a at the time t1 and t2. The power $\overline{\Delta P}$ by this torque is expressed by the formula, $\overline{\Delta P} = 1.027 \cdot \overline{\Delta T} \cdot \overline{N}$ where $\overline{N}$ represents the average rotational speed of the pedal 1a during the time interval between the time t1 and the time t2.

The above considerations are related to the power contributing to the increase of the inertia energy, and the torque acting against the brake torque is different from the power. With respect to the power P against the brake torque, if the brake torque during the time interval between the time t1 and the time t2 is constant and is the brake torque $T_0$ at the time t1, there is established $P_0 = 1.027 \, T_0 \cdot \overline{N}$. Therefore, the total power is represented in the following:

$$P = 1.027 T_0 \cdot \overline{N} + 1.027 \cdot \overline{\Delta T} \cdot \overline{N}$$

In the above manner, the total power is found for each transition of the pedal from the upper dead point U to the lower dead point L occurring during 4 to 5 seconds after the start of the pedaling, and the peak power during the above 4 to 5 seconds is found.

B. Determination of Time t1 and Time t2

As described above, for determining the total power P, the times t1 and t2 which satisfy $\Delta T = 0$ must be determined. In this embodiment, a mid point between the time point when the differential of the rotational speed of the pedal 1a, that is, the time differential dN (FIG. 4(B)), takes the minimal value and the time point when it takes the maximal value is determined as the time t1. And, a mid point between the time point of the next maximal value and the time point of the next minimal value is determined as the time t2.

As shown in FIG. 6, it is thought that the differential of the rotational speed usually becomes minimum at the upper dead point U and at the lower dead point L, and it is also thought that the differential of the rotational speed becomes maximum at the horizontal angle. Since a negative bias corresponding to the brake torque is encountered, it is preferred that the time t1 be behind the upper dead point U and that the time t2 be ahead of the lower dead point L. Therefore, the mid point between the time point when the differential of the rotational speed of the pedal 1a, that is, the time variation dN (FIG. 4(B)), takes the minimal value and the time point when it takes the maximal value is determined as the time t1. And, the mid point between the time point of the next maximal value and the time point of the next minimal value is determined as the time t2.

It has been found that such approximation is well adapted for the actual data.

For a better understanding, the time intervals between t1 and t2 are indicated by $\Delta t0$, $\Delta t1$, $\Delta t2$ . . . in FIG. 4.

C. Correction by Regression Formula

As described in the measurement principle, the inertia power $\overline{\Delta P}$ is a function of $\Delta N / \Delta t$. Due to the unstableness resulting from the pedaling motion and also due to the unstableness occurring immediately after the start of the pedaling, the two vary independently of each other, so that it may be difficult to perform an accurate measurement.

Therefore, in this embodiment, $\Delta N$ and $\Delta t$ are regressed by the average rotational speed $\overline{N}$ of the pedal 1a during the measurement period of 4 to 5 seconds, and utilizing each regression formula, the inertia power is obtained as the function of the average rotational speed, thereby determining the peak power.

It has been found through experiments that the regression formulas of $\Delta N$ and $\Delta t$ are both hyperbolic functions. Considering the fact that the initial values of $\Delta N$ and $\Delta t$ are particularly unstable (see FIG. 4(B)), the initial values are neglected or ignored, and as a result the two regression formulas are linear formulas. Therefore, in specific examples, the linear regression formulas are used.

Figure 7A:
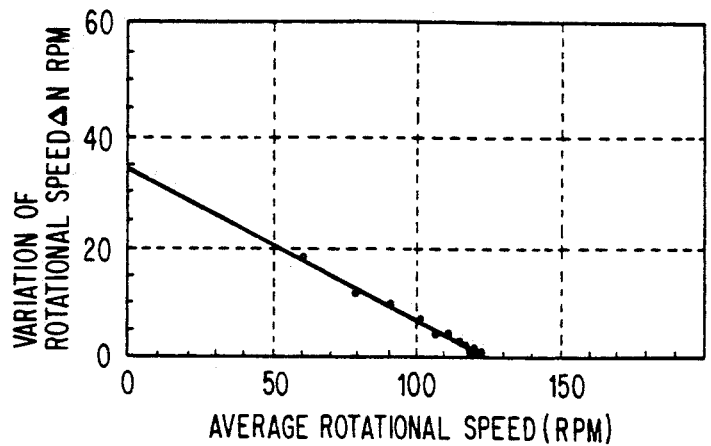
Figure 7B:
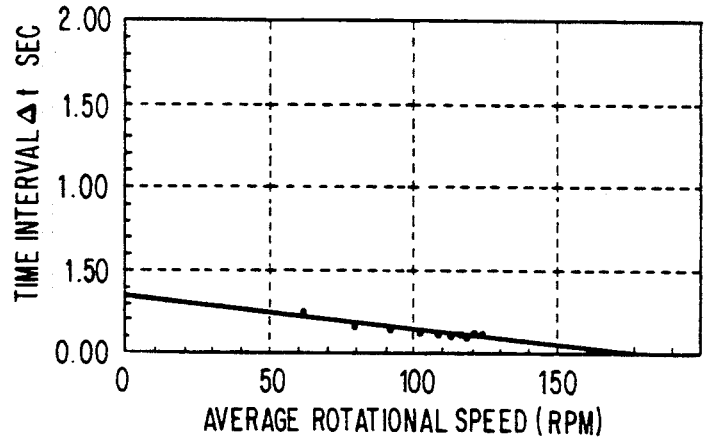
Figure 7C:
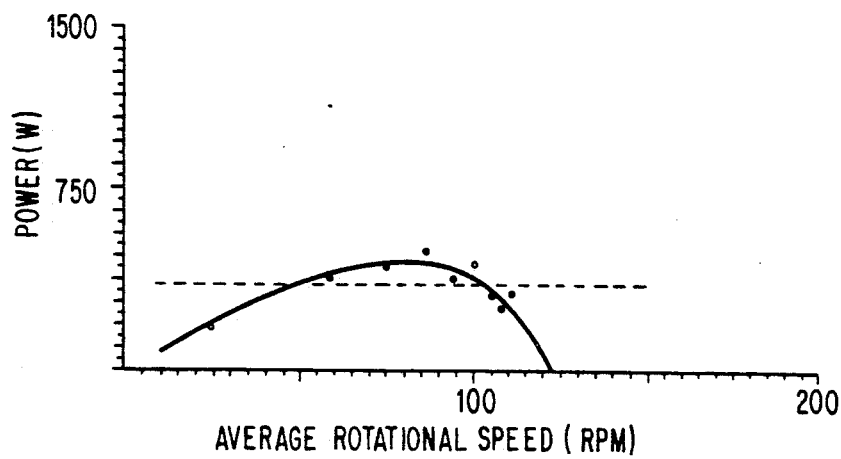

Examples of the actual or measured values and regression formulas of the $\Delta N$ and $\Delta t$ are shown in FIGS. 7(A) and 7(B), respectively. In FIG. 7(C), a solid line indicates the power calculated from the above two regression formulae, and by finding its peak power, the appraisal value can be determined.

In this figure, a broken line indicates the average power determined by the actual values, and shows a simplified appraisal value.

D. Measures Against Noises

In order to extract the characteristics or trend of the rotational speed of the pedal 1a, a filtering process is performed in this embodiment. Specifically, a motion averaging process is repeated five times.

E. Selection of Brake Torque

The brake torque may be zero. In this case, the total power is composed only of the inertia power. Also, it may be a constant torque or a ramp waveform. The subjects are classified according to age, sex and preducted power, and the brake torque is selected according to the class. With this procedure, a more accurate measurement can be expected.

Further, by selecting the brake torque in the following manner so as to simulate a running motion, its instantaneous power can be determined.

Namely, the brake torque is selected to satisfy the following formula:

$$T_l = J' \frac{d\omega}{dt} \quad (4)$$

As described above, the following is obtained:

$$J_0 \cdot \frac{d\omega}{dt} = T - T_l \quad (5)$$

From the formulas (4) and (5), the following is obtained:

$$(J_0 + J') \frac{d\omega}{dt} = T$$

Further, the following is obtained:

$$\frac{1}{r^2} J_m \frac{dv}{dt} = f$$

where $J_m = J_0 + J'$: pseudo inertia load.

Here, using $\omega = v/r$ and $T = r \cdot f$, the following is obtained:

$$(1/r^2) \cdot (J_0 + J') dv/dt = f$$

where r represents the length (m) of the crank, v represents the peripheral speed (m/s) of the pedal, and f represents the force [kg] in the direction of rotation of the pedal.

This formula is an equation of exercise taken when a person having the body weight M [kg] = $(1/r^2) \cdot (J_0 + J)$ runs.

$J_0/r^2$ is an equivalent body weight $m_0$ [kg] calculated from the substantial inertia moment. Therefore, if $J'$ is represented by $J' = r^2(M - m_0)$, the running exercise of each subject having body weight M can be simulated.

Specifically, the difference dN of the rotational speed for each sampling interval dt is found from the formula (4), and the applied load is determined from $J'$ and $2\pi/60 \cdot dN/dt$.

F. Specific Example of Construction

Next, the specific construction of this embodiment will now be described.

Figure 2:
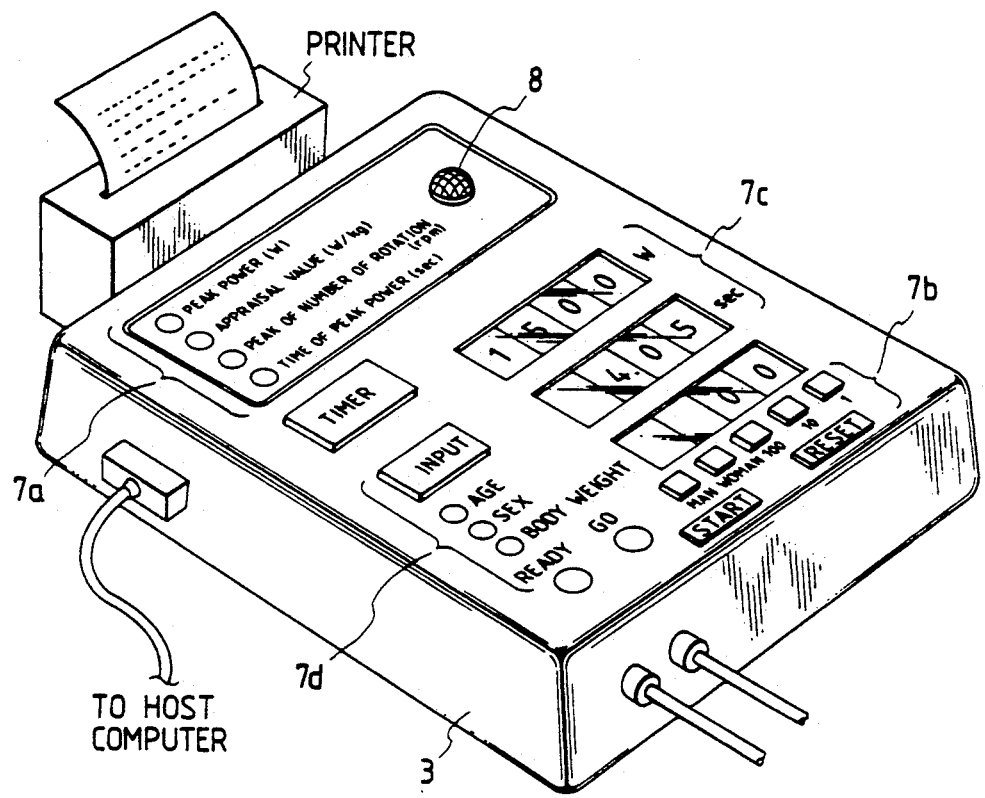
FIG. 2 is a plan view showing a panel of a control box of FIG. 1.
Figure 3:
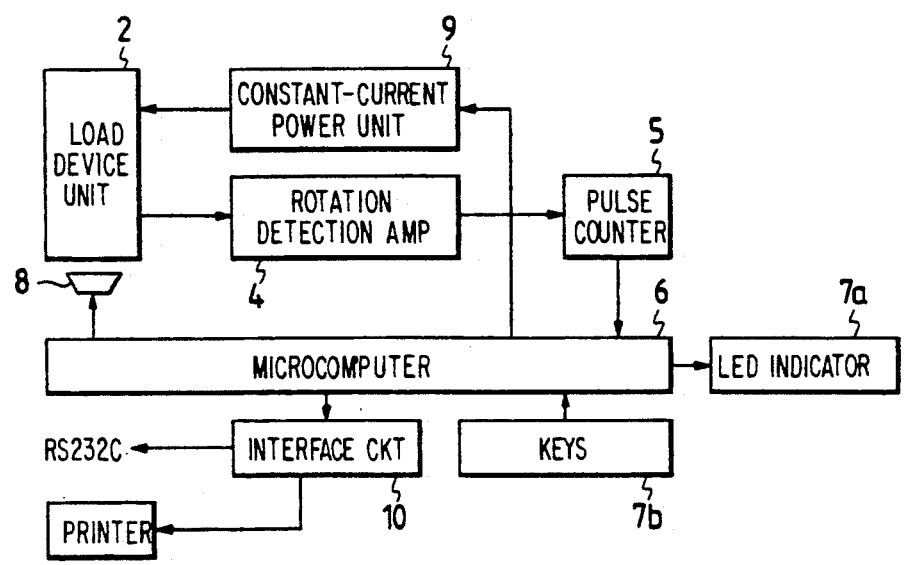
FIG. 3 is a block diagram of one example of circuitry of the embodiment of FIG. 1.

FIG. 2 shows a panel of the control box 3 of FIG. 1, and FIG. 3 shows the construction of a circuitry associated with the control box 3.

Referring to FIG. 2, a measurement result display 7a, a measurement result option-switching switch 7b, a timer indicator 7c, switches 7d (an input switch, an input confirmation switch, a start switch, a reset switch, a ready switch), a buzzer 8 and so on are mounted on the panel of the control box 3.

The subject operates the panel to set input parameters, and performs the pedaling at full power for 4 to 5 seconds, seeing a pedaling start display and a timer indication. Then, the subject recognizes the measurement results through the display or a printed sheet.

Figure 8:
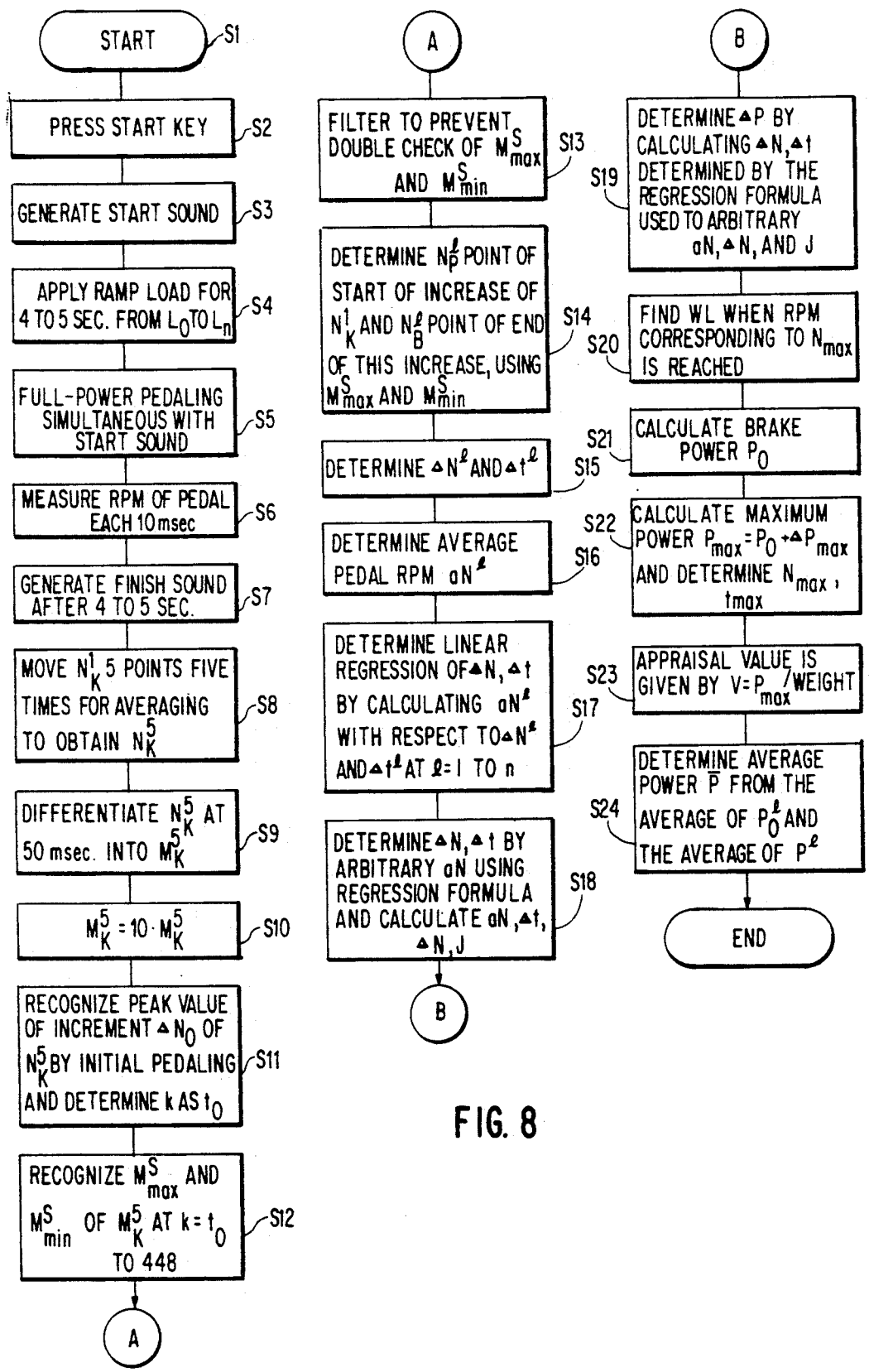
FIG. 8 is a flow chart for explaining the operation of the embodiment of FIG. 1.

In FIG. 3, rotation detection pulses are fed from the load device unit 2 to a pulse counter 5 via a detection amplifier 4 where the input pulses for each sampling interval are counted, and the counter feeds to a microcomputer 6 digital data corresponding to the rotational speed of the pedal 1a. The inputs from the various switches 7b are also supplied to the microcomputer 6 through key operation, and in accordance with these inputs, computation or processing shown in a flow chart of FIG. 8 is carried out, and the measurement results of the instantaneous power are displayed in the measurement result display 7a. The microcomputer 6 also supplies a brake torque-controlling analog signal to a constant-current power unit 9 so as to control the load device unit 2. Further, the microcomputer 6 is connected to a host computer via an interface circuit 10, so that the management of the measurement results, etc., can be made.

G. Flow of Operation

Next, the operation of the construction of FIG. 3 will now be described with reference to FIG. 8. A summary of the steps of FIG. 8 are as follows:

S1: Start
S2: Press start key
S3: Generate start sound
S4: Apply ramp load for 4 to 5 sec. from $L_0$ to $L_n$
S5: Full-power pedaling simultaneous with start sound
S6: Measure rpm of pedal each 10 msec.
S7: Generate finish sound after 4 to 5 sec.
S8: Move Nk' 5 points five times for averaging to obtain $Nk^5$
S9: Differentiate $Nk^5$ at 50 msec into $Mk^5$
S10: $Mk^5 = 10 \, Mk^5$
S11: Recognize peak value of increment $\Delta N_0$ of $Nk^5$ by initial pedaling and determine k as $t_0$
S12: Recognize $M^5max$ and $M^5min$ of Mk at k=$t_0$ to 448
S13: Filter to prevent double check of $M^5max$ and $M^5min$
S14: Determine $N_P'$ point of start of increase of Nk' and $N_B'$ point of end of this increase, using $M^5max$ and $M^5min$
S15: Determine $\Delta N^l$ and $\Delta t^l$
S16: Determine average pedal rpm $aN^l$
S17: Determine linear regression of $\Delta N$, $\Delta t$ by calculating $aN^l$ with respect to $\Delta N^l$ and $\Delta t^l$ at $l=1$ to n
S18: Determine $\Delta N$, $\Delta t$ by arbitrary $aN$ using regression formula and calculate aN, $\Delta t$, $\Delta N$, J.
S19: Determine $\Delta P$ by calculating $\Delta N$, $\Delta t$ determined by the regression formula used to arbitrary aN, $\Delta N$, and J
S20: Find WL when rpm corresponding to Nmax is reached
S21: Calculate brake power $P_0$
S22: Calculate maximum power Pmax = $P_0 + \Delta$Pmax and determine Nmax, tmax
S23: Appraisal value is given by V = Pmax/weight
S24: Determine average power P from the average of $P_0^l$ and the average of $P^l$.

Steps S1 to S6

In these steps, the subject performs the pedaling at full power for 4 to 5 seconds, and the rotational speed of the pedal 1a a during that time is measured at sampling intervals of 10 milliseconds. In this example, a brake load WL is a ramp load, and varies as follows:

$$WL[kgm] = L_0 + \Sigma_{i=1}^{90} \frac{(L_n - L_0) \cdot i}{90}$$

where i increments each 50 millisecond in the range of 1 to 90, and $L_0$ and $L_n$ are 1 kgm and 4 kgm, respectively.

$N_k^l$ in Step S6 is the measurement value at each 10 millisecond interval, and k increments each 10 millisecond in the range of 1 to 450.

Step S8

This Step deals with the noise elimination process, and the nth average process $N_k^{n+1}$ is executed in the following manner:

$$N_k^{n+1} = \frac{1}{5}(\Sigma_{l=-2}^{l=+2} N_{k+L}^n)$$

where k=3 to 448, n=1 to 4.

Steps S9 to S10

In these Steps, differentiating processes are carried out. The differentiation is carried out according to $M_k^5 = N_{k+5}^5 - N_k^5$, and in order to bring this into the same recognition level as $N_k^5$, the amplification is carried out according to $M_k^5 = 10 \cdot M_k^5$.

Step S11

The initial time $t_o$ is determined. The differential value M at the time of the start of the pedaling includes many noises and cannot be recognized, and therefore the following is provided:

$$-0.5 < N_{k-l-1}^5 - N_{k-l}^5 < 0.5$$

With respect to k in the case of l=0 to 4, k is determined as $t_0$ when $N_{k-10}^5 - N_k^5 < -1$ is established with respect to k provided by previous condition.

Steps S12 to S13

The maximum and the minimum of the differential value are recognized. In Step S12, with respect to $K = t_0$ to 448, $M_k^5$ is determined as the first minimal value $M^1\min = M_k^5$ when $M_k^5 < M_{k+L}^5$ is established with respect to l= −2 to +2, and k obtained at this time is determined as t1.

The second minimal value $M^2\min$ is found with respect to k=t1 to 448, and similarly n minimal values $M^s\min$ (S=1 to n) are found.

With respect to k=$t_0$ to 448, $M_k^5$ is determined as the first maximal value $M^1\max = M_k^5$ when $M_k^5 > M_{k+L}^5$ is established with respect to L= −2 to +2, and k obtained at this time is determined as t1.

The second maximal value $M^2\max$ is found with respect to k=t1 to 448, and similarly n' maximal values $M^s\max$ (S=1 to n') are found.

In the checking of the maximal value in Step S13, first, $N_{ks}^5$ at $M^s\max$ is obtained, and $N_{ks+1}^5$ at $M^{s+1}\max$ is obtained. And, $M^{s+1}\max$, obtained when $-1 < N_{ks+1}^5 - N_{ks}^5 < 1$ is obtained with respect to S=1 to n, is removed as a recognition mistake.

Similarly, the check with the minimal values are carried out with respect to n' $M^s$mins.

Step S14

Here, first, the times of the maximal value and the minimal value are found.

k at $M^1\min$ is determined at k1.
k at $M^1\max$ is determined at k2.
k at $M^2\min$ is determined at k3.
...
...
...
k at $M^{n-1}\min$ is determined as $k_{3(n-1)+1}$.
k at $M^{n-1}\max$ is determined as $k_{3(n-1)+2}$.
k at $M^n\min$ is determined as $k_{3(n-1)+3}$.
However,
$M^s\min \ldots S = 1$ to n.
$M^s\max \ldots S = 1$ to n'.

Thereafter, using these times inflection points t1 and t2 shown in FIG. 5 are found. These are substituted at the following mid points, respectively.

$$k^l\min = \tfrac{1}{2}[k_{3(l-1)+2} - k_{3(l-1)+1}] + k_{3(l-1)+1}$$

$$k^l\max = \tfrac{1}{2}[k_{3(l-1)+3} - k_{3(l-1)+2}] + k_{3(l-1)+2}$$

where l=1 to n.

Then, the peak value and the bottom value of the rotational speed of the pedal 1a are determined as follows:

$N_B^l = N^1 \cdot k^l\min$ ... The value of $N^1$ at time $k^l\min$.
$N_P^l = N^1 \cdot k^l\max$ ... The value of $N^1$ at time $k^l\max$

Step S15

Here, the following calculation is made:

$$\Delta N^l = N_P^l - N_B^l$$

$$\Delta t^l = (K_{max}^l - K_{min}^l)10_{(ms)} \cdot \frac{1}{1000_{(ms)}}$$

where l=1 to n.

Step S16

Here, the following calculation is made:

$$aN^l = N^l \cdot K_a^l \ldots \text{The value of } N^l \text{ at time } k_a^l$$

$$k_a^l = \frac{1}{2}(K_{max}^l - K_{min}^l) + K_{min}^l$$

Step S17

The following is calculated:

$$\Delta N = b_1 \cdot aN + b_0$$

$$\Delta t = c_1 \cdot aN + c_0$$

Step S18

The inertia power is calculated as follows:

$$\Delta P = 1.027 \times aN \times \frac{2\pi}{60} J \frac{\Delta N}{\Delta t}$$

Step S19

The processing here is as shown in the block diagram.

Step S20

The following calculation is made, using k at $N_k' = N_{max}$ as $k_{max}$:

$$WL = L_0 + \Sigma_{i=1}^{kmax} \frac{(L_n - L_0) \cdot i}{90}$$

Step S21

The following is calculated:

$$P_0 = 1.027 \cdot WL \times N_{max}$$

Step S22

The following is calculated:

$$t_{max} = 10_{(ms)} \cdot K_{max} \frac{1}{1000_{(ms)}}$$

In the block diagram, the maximum rotational speed when $P_{max}$ is obtained is indicated as $N_{max}$, and the time when $P_{max}$ is obtained is indicated as $t_{max}$.

Step S23

Here, according to the power theory, the power is proportional to the body weight, and therefore the $P_{max}$ is divided by the body weight of each subject as shown in the block diagram, thereby obtaining a relative appraisal value.

Step S24

Here, $\overline{P_0}$, that is, the average of each $P_0^l$ at $t^l$, and $\overline{\Delta P}$, that is, the average of each $\Delta P^l$ at $\Delta N$ and $\Delta t$ are found, and the following is obtained:

$$\overline{P} = \overline{P_0} + \overline{\Delta P}(L = 1 \text{ to } n)$$

The average $\overline{P}$ thus obtained is a simplified appraisal power of the measurement shown in FIG. 7(C).

As described above, according to the present invention, the instantaneous power can be measured through a full-power pedaling of a quite short time, and a physical burden on the subject is small. In addition, since the appraisal is based on the peak value obtained around 2 seconds after the star of the pedaling, this is the optimum appraisal for the instantaneous power. Further, by using the regression formula, a more stable and highly accurate appraisal can be made. Since the bicycle ergometer is utilized, the subject can easily make the measurement, and there is no problem from the viewpoint of safety. Because of the analogousness to a running motion, this is used for substitution for the instantaneous power in the running motion. Further, by adjusting the brake torque, the measurement can be performed in a wide variety of forms.

What is claimed is:

1. A method of measuring instantaneous power exerted on a rotary member thru pedaling a bicycle ergometer, comprising the steps of:
   repeatedly measuring the rotational speed of said rotary member at short time intervals when said rotary member is rotated by pedaling said bicycle ergometer equipped with an inertia mechanism having an inertia with respect to a rotational driving movement;
   detecting said rotational speed at each point of start of increase of said rotational speed and at each point of end of increase of said rotational speed, said start and end points alternatingly occurring;
   measuring the lapsed times from each said point of start of increase to succeeding said point of end of increase;
   finding a finite difference of said lapsed times;
   finding the differences of the rotational speeds from said points of start of increase to said points of end of increase during said lapsed times, respectively;
   finding, as an average rotational speed, the rotational speed at a mid point between said point of start of increase and said point of end of increase;
   finding a regression formula with respect to said average rotational speed of the alternating differences of said lapsed time;
   finding a regression formula with respect to said average rotational speed of the alternating differences of said rotational speed;
   and obtaining power with respect to said inertia mechanism in accordance with said two regression formulas, said power being obtained as a function of said average rotational speed.

2. The method of measuring instantaneous power according to claim 1, in which said rotational speed is subjected to a filtering process to remove noises.

3. The method of measuring an instantaneous power according to claim 2, in which said filtering process is one or more movement average processes.

4. The method of measuring instantaneous power according to any one of claims 1 to 3, in which a first judgment with respect to said point of start of increase of the rotational speed and said point of end of increase thereof immediately after the start of the pedaling is ignored.

5. The method of measuring instantaneous power according to any one of claims 1 to 3, in which a mid point between a time point of the minimal value of the time difference of said rotational speed and a time point of the next maximal value thereof is determined as said point of start of increase of the rotational speed, a mid point between said time point of the maximal value and a time point of the next minimal value being determined as said point of end of increase of the rotational speed.

6. The method of measuring instantaneous power according to any one of claims 1 to 3, in which the maximum value of the power with respect to said inertia mechanism is found from said regression formula for the difference of the rotational speed and the regression formula for the difference of the lapsed time, and is determined as an appraisal value of the instantaneous power for the power with respect to said inertia mechanism.

7. The method of measuring an instantaneous power according to any one of claims 1 to 3, in which said bicycle ergometer includes a brake mechanism capable of applying a brake torque.

8. The method of measuring instantaneous power according to claim 7, in which the power with respect to said brake mechanism is added to the power with respect to said inertia mechanism, thereby obtaining the total power.

9. The method of measuring instantaneous power according to claim 8, in which the maximum value of the power with respect to said brake power at said average rotational speed at which the power with respect to said inertia mechanism is added to the power with respect to said inertia mechanism, thereby obtaining an appraisal value of the total instantaneous power.

10. The method of measuring an instantaneous power according to claim 9, in which the appraisal value of the total instantaneous power is divided by the body weight of the subject to make a correction.

11. The method of measuring an instantaneous power according to any one of claims 1 to 3, in which an alarm is given before the chemical energy in a non-lactic acid-type anoxia mechanism is exhausted after the start of the pedaling of said bicycle ergometer.

12. The method of measuring an instantaneous power according to claim 11, in which said alarm is given within 5 seconds after the start of the pedaling.

13. A method of measuring instantaneous power comprising the steps of:

repeatedly measuring the rotational speed of a rotary member at short time intervals when said rotary member is rotated by pedaling a bicycle ergometer equipped with an inertia mechanism having an inertia with respect to a rotational driving movement;

detecting said rotational speed at each point of start of increase of said rotational speed and at each point of end of increase of said rotational speed, said start and end points alternatingly occurring;

measuring a difference of a lapsed time from said point of start of increase to said point of end of increase;

finding a difference of the rotational speed from said point of start of increase to said point of end of increase during said lapsed time;

finding, as an average rotational speed, the rotational speed at a mid point between said point of start of increase and said point of end of increase;

calculating, during each repeated cycle between said point of start of increase and said point of end of increase, power with respect to said inertia mechanism in accordance with the differential of the rotational speed and the average rotational speed corresponding to each repeated cycle.

14. Apparatus for measuring instantaneous power comprising:

a bicycle ergometer body equipped with an inertia mechanism having an inertia with respect to a rotational driving movement;

means for measuring a rotational speed of a rotary member of said bicycle ergometer at predetermined time intervals;

calculating means responsive to the measurement value of the rotational speed for finding a lapsed time between a point of start of increase of the rotational speed and a point of end of increase thereof, and a difference of said lapsed time, and for finding, as an average rotational speed, the rotational speed at a mid point between said point of start of increase and said point of end of increase during said lapsed time, said calculating means determining the power with respect to said inertia mechanism in accordance with the above calculated values;

means for indicating said calculated values determined by said calculating means;

a timer for indicating the time of the pedaling; and alarm means for giving an alarm when the set time of said timer is over.

15. Apparatus for measuring instantaneous power according to claim 14, in which said calculating means finds a regression formula with respect to the average rotational speed of the difference of said lapsed time as well as a regression formula with respect to the average rotational speed of the difference of said rotational speed, said calculating means obtaining the power with respect to said inertia mechanism as a function of said average rotational speed, and calculating the maximum value of the power with respect to said inertia mechanism.

16. Apparatus for measuring instantaneous power according to claim 14, in which said bicycle ergometer is provided with a brake mechanism.

17. Apparatus for measuring instantaneous power according to claim 16, in which said calculating means calculates the power with respect to said brake mechanism when the power with respect to said inertia mechanism becomes the maximum, and adds it to the maximum value of the power with respect to said inertia mechanism, thereby providing an appraisal value of the instantaneous power.

18. Apparatus for measuring instantaneous power according to claim 17, in which said calculating means divides said appraisal value of said instantaneous power by the body weight of the subject to make a correction.

19. Apparatus for measuring an instantaneous power according to any one of claims 14 to 18, in which said bicycle ergometer body is provided with a fastening means for fixing the subject to a saddle so that the subject cannot stand-up.

* * * * *